United States Patent
Linder

(10) Patent No.: US 9,562,046 B2
(45) Date of Patent: *Feb. 7, 2017

(54) MEANS AND METHOD FOR TREATING SOLID TUMORS

(71) Applicant: Vivolux AB, Mölndal (SE)

(72) Inventor: Stig Linder, Bromma (SE)

(73) Assignee: VIVOLUX AB, Mölndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/435,707

(22) PCT Filed: Sep. 17, 2013

(86) PCT No.: PCT/SE2013/000142
§ 371 (c)(1),
(2) Date: Apr. 14, 2015

(87) PCT Pub. No.: WO2014/046589
PCT Pub. Date: Mar. 27, 2014

(65) Prior Publication Data
US 2015/0259349 A1  Sep. 17, 2015

(30) Foreign Application Priority Data
Sep. 21, 2012 (SE) ..................... 1220571

(51) Int. Cl.

| | | |
|---|---|---|
| C07D 487/04 | (2006.01) | |
| C07D 401/12 | (2006.01) | |
| A61K 31/53 | (2006.01) | |
| A61K 31/519 | (2006.01) | |
| A61K 31/4985 | (2006.01) | |
| A61K 31/4427 | (2006.01) | |
| A61K 31/407 | (2006.01) | |
| A61P 35/00 | (2006.01) | |
| C07D 471/04 | (2006.01) | |
| A61K 45/06 | (2006.01) | |
| A61K 31/365 | (2006.01) | |
| A61K 31/366 | (2006.01) | |
| A61K 31/4706 | (2006.01) | |
| A61K 31/475 | (2006.01) | |
| A61K 31/7076 | (2006.01) | |
| A61K 31/444 | (2006.01) | |

(52) U.S. Cl.
CPC ........... *C07D 487/04* (2013.01); *A61K 31/365* (2013.01); *A61K 31/366* (2013.01); *A61K 31/444* (2013.01); *A61K 31/475* (2013.01); *A61K 31/4706* (2013.01); *A61K 31/519* (2013.01); *A61K 31/53* (2013.01); *A61K 31/7076* (2013.01); *A61K 45/06* (2013.01); *C07D 401/12* (2013.01); *C07D 471/04* (2013.01)

(58) Field of Classification Search
CPC ... C07D 487/14; C07D 401/12; A61K 31/407; A61K 31/4427; A61K 31/4985; A61K 31/519; A61K 31/53

USPC ... 544/184, 250, 345; 546/82; 514/243, 249, 514/267, 293
See application file for complete search history.

(56) References Cited

U.S. PATENT DOCUMENTS

| | | | |
|---|---|---|---|
| 4,831,038 A | 5/1989 | Trouet et al. | |
| 5,480,906 A | 1/1996 | Creemer et al. | |
| 2003/0092716 A1 | 5/2003 | Almstead et al. | |
| 2012/0095045 A1 | 4/2012 | Yeo | |
| 2014/0073645 A1* | 3/2014 | Linder .................. A61K 45/06 514/243 |

FOREIGN PATENT DOCUMENTS

| | | |
|---|---|---|
| WO | 99/02143 A2 | 1/1999 |
| WO | 02/089809 A1 | 11/2002 |
| WO | 2006/055412 A1 | 5/2006 |
| WO | 2006/113703 A2 | 10/2006 |
| WO | 2007/128820 A1 | 11/2007 |
| WO | 2008/127715 A1 | 10/2008 |
| WO | 2009/035534 A2 | 3/2009 |
| WO | 2012/128689 A1 | 9/2012 |

OTHER PUBLICATIONS

Cecil Textbook of Medicine, edited by Bennet, J.C., and Plum F., 20th edition, vol. 1, 1004-101 O, 1996.*
Wolff Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
Gavhane Y. N. et al. International Journal of Pharma Sciences and Research (IJPSR) vol. 2(1), 2011, 1-12.*
Eshba et al, Pharmazie, 42(10):664-666 (1987).
Sasaki, Chloroquine Potentiates the anti-cancer effect of 5-fluorouracil on colon cancer cells, BMC Cancer 2010, 10:370 (11 pages).

(Continued)

*Primary Examiner* — Venkataraman Balasubramanian
(74) *Attorney, Agent, or Firm* — Porter Wright Morris & Arthur LLP

(57) ABSTRACT

In a cytotoxic compound of the general formula (I) R is H or methyl or methylene substituted by $C_1$-$C_4$ straight or branched alkyl, $R^1$ is selected from the group consisting of H, $C_1$-$C_4$ straight or branched alkyl, methoxy, methoxy substituted by from one to three fluorine, halogen; $R^2$ is H or $C_1$-$C_4$ straight or branched alkyl; X is CH or N; Y is CH or N.

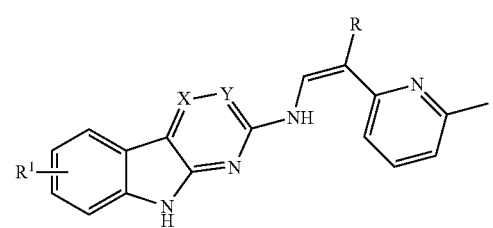

(I)

17 Claims, 3 Drawing Sheets

(56) References Cited

OTHER PUBLICATIONS

Bredel-Geissler et al, Proliferation-Associated Oxygen Consumption and Morphology of Tumor Cells in Monolayer and Spheroid Culture, Journal of Cellular Physiology, 153:44-52 (1992).
Freyer et al, In Situ Oxygen Consumption Rates of Cells in V-79 Multicellular Spheroids During Growth, Journal of Cellular Physiology, 118: 53-61 (1984).
Kunz et al, "Oncogene-Associated Growth Behavior and Oxygenation of Multicellular Spheroids from Rat Embryo Fibroblasts", Oxygen Transport to Tissue XV, P. Vaupel, Editor, Plenum Press, New York, pp. 359-366, (1994).
Sutherland et al, Radiation Response of Multicell Spheroids an in Vitro Tumour Model, Current Topics in Radiation Research Quarterly, 11: 87-139 (1976).

\* cited by examiner

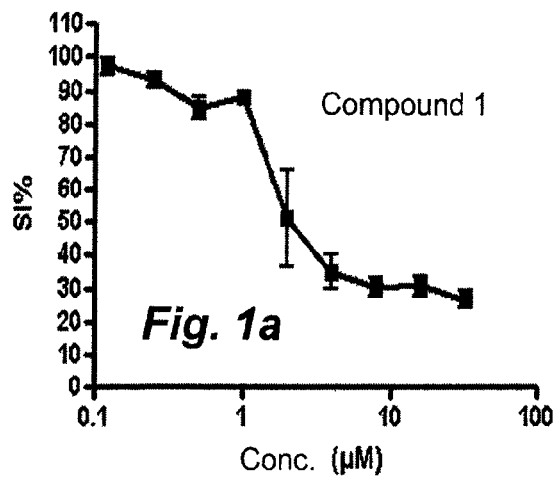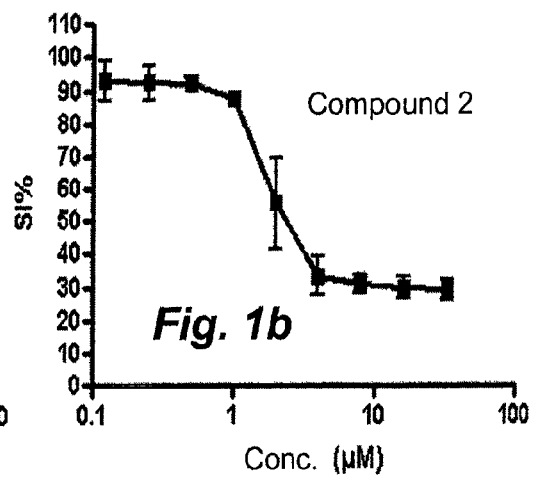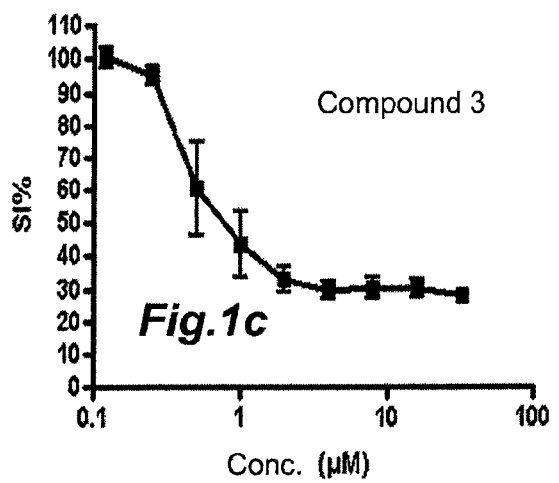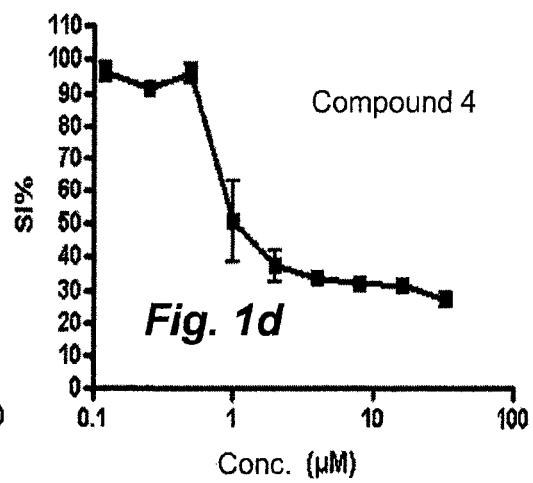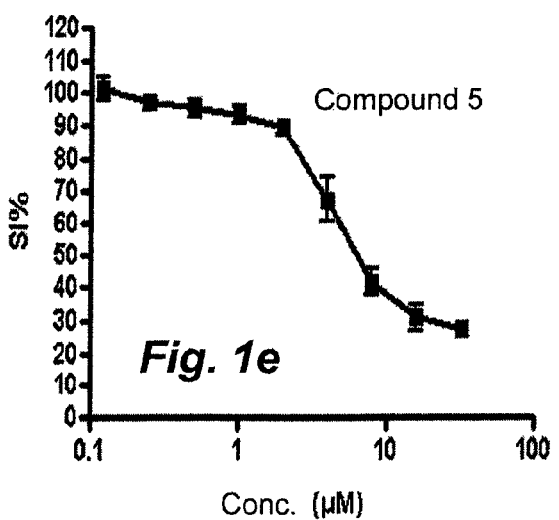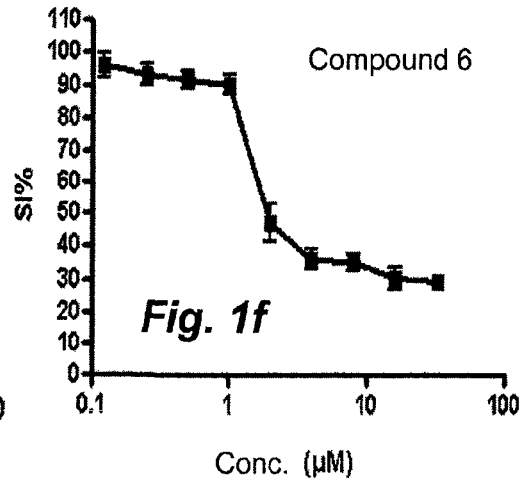

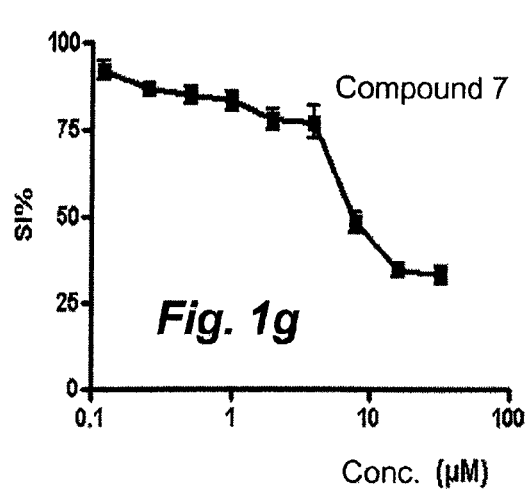
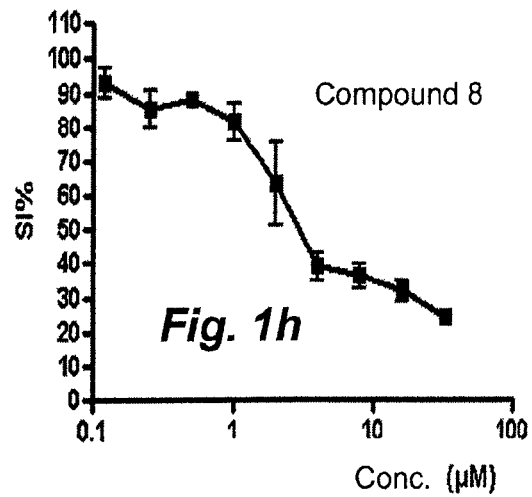
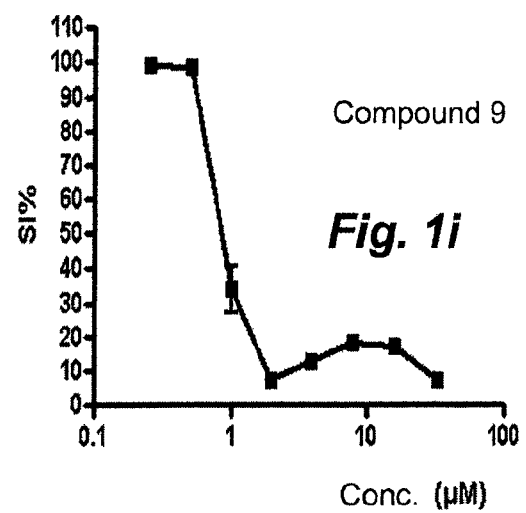
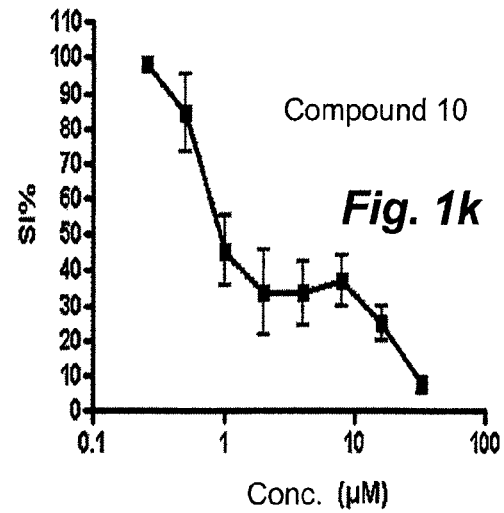
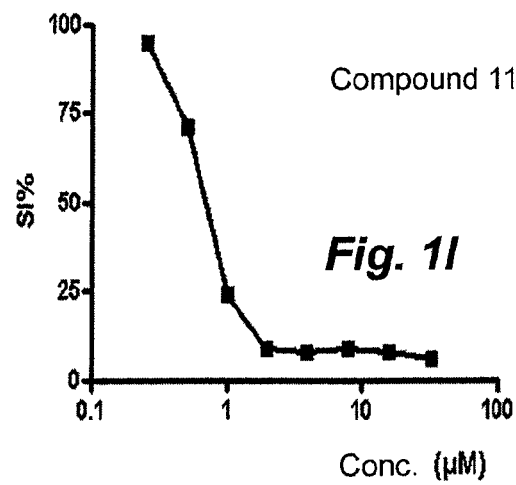

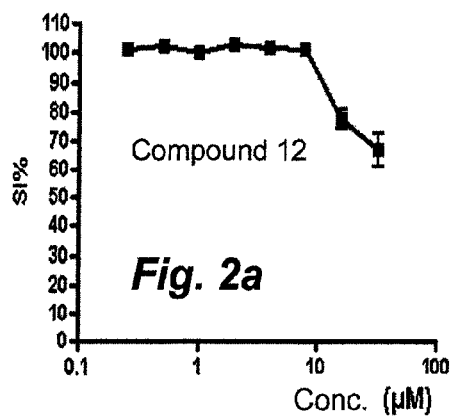
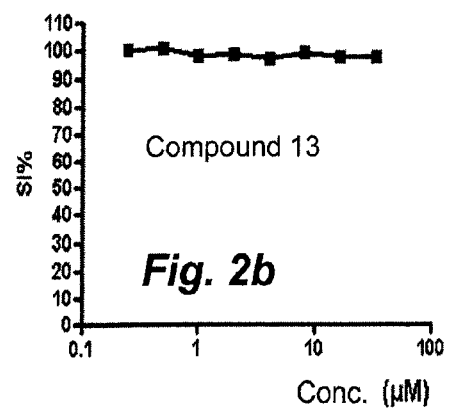
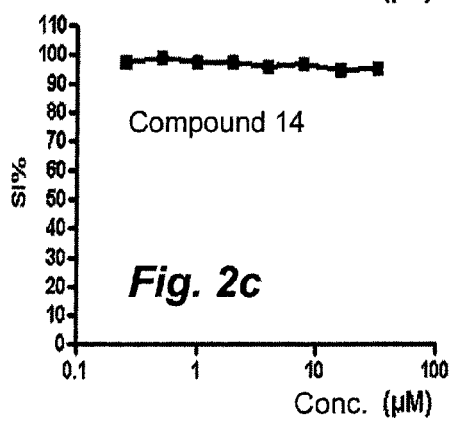
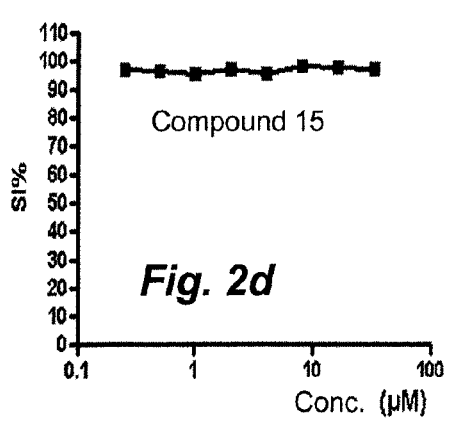
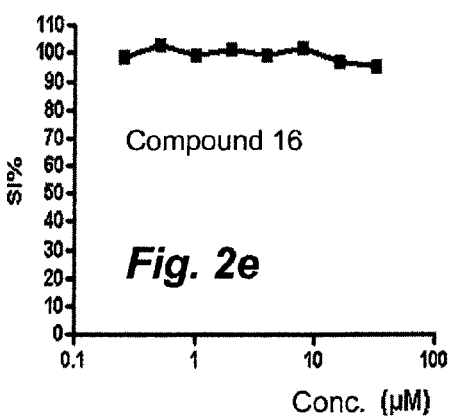
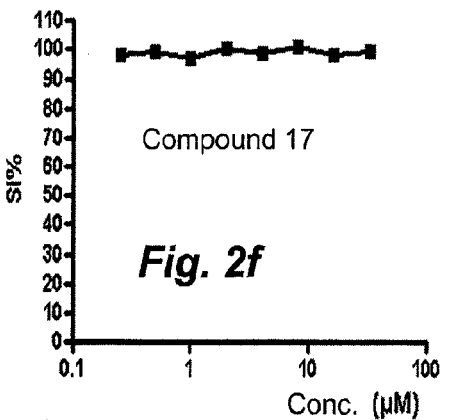
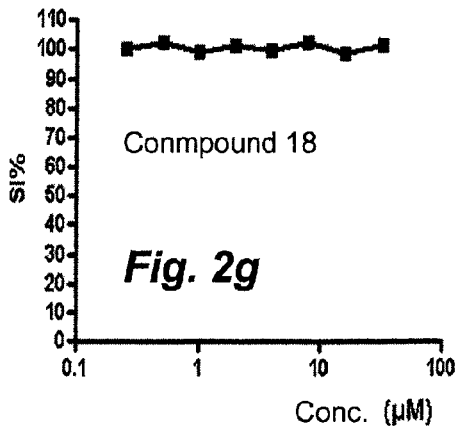
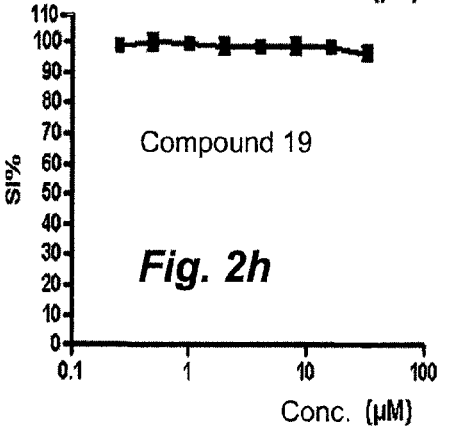

MEANS AND METHOD FOR TREATING SOLID TUMORS

FIELD OF THE INVENTION

The present invention relates to a means for treating solid cancer tumours, in particular disseminated solid cancer tumours, in a person affected by cancer and to a corresponding method.

BACKGROUND OF THE INVENTION

New and effective anticancer drugs need to be developed for patients that suffer from disseminated cancer. Developing drugs for solid tumours is associated with specific problems due to complex biophysical and metabolic conditions in 3-D tumour tissue which may be difficult to mimic in experimental in vitro systems. Hypoxia and limited diffusion of nutrients is known to lead to quiescence and resistance to conventional anticancer agents and radiation therapy. Furthermore, anticancer drugs must be able to penetrate into tumour parenchyme to reach cancer cells at toxic concentrations. Some drugs that are in clinical use for the treatment of solid tumours show poor penetration into 3-D tumour masses, which may be one of the reasons for their limited efficacy. Multicellular spheroids (MCS) mimic human solid tumours better than 2-D monolayer cultures and, therefore, are better suited than monolayer cultures for screening drugs active on solid tumours.

Cell death is often subdivided into three types of cell death: apoptosis (type I), autophagic cell death (type II) and necrosis (type III). Apoptosis is mediated by the activation of caspases. Autophagy is an evolutionarily conserved mechanism for degradation of long-lived cellular proteins and damaged cell organelles. The formation of autophagosomes is a main characteristic of autophagy. Autophagosome formation requires activation of class III phosphatidylinositol-3-kinase and is also dependent of two ubiquitin-like conjugation systems (Atg-Atg12 and Atg8). Autophagy protects cells during conditions of nutrient deprivation, and cells undergo apoptosis when autophagy is inhibited. Morphological features of autophagy have also been observed during cell death under conditions of caspase inhibition.

OBJECTS OF THE INVENTION

A primary object of the invention is to provide a means for efficient treatment of solid cancers tumours.

A further object of the invention is to provide a therapeutic method employing the means.

Other objects of the invention will become evident from the following summary of the invention, a number of preferred embodiments thereof illustrated in a drawing, and the appended claims.

SUMMARY OF THE INVENTION

According to the invention is disclosed a means for efficient treatment of solid cancer tumours. The means is a compound of the general formula I, wherein R is H or methyl or methylene substituted by $C_1$-$C_4$ straight or branched alkyl, $R^1$ is selected from the group consisting of H, $C_1$-$C_4$ straight or branched alkyl, methoxy, methoxy substituted by from one to three fluorine, halogen; $R^2$ is H or $C_1$-$C_4$ straight or branched alkyl; X is CH or N; Y is CH or N; R does not comprise H or methyl if $R^1$ is H or $C_1$-$C_4$ alkyl, $R^2$ is H or $C_1$-$C_4$ straight or branched alkyl, X is N and Y is N.

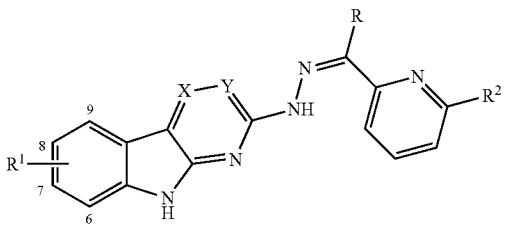

It is preferred for $R^2$ to be H. Preferred embodiments of the compound of the invention comprise R=H, $R^1$=6-$CH_3$, $R_2$=H, X and Y=CH; R=$CH_2C(CH_3)_3$, $R^1$=6-$CH_3$, $R_2$=H, X and Y=N; R=$CH_2CH_3$, $R^1$=6-$CH_3$, $R_2$=H, X and Y=N.

According to a preferred aspect of the invention the compound of the general formula may be additionally substituted by $C_1$-$C_4$ straight or branched alkyl at one of positions 6, 7, 8, 9 of the mono-, di- or tri-azacarbazolyl not substituted by $R^1$.

The compound of the invention comprises any pharmaceutically acceptable salt, salt/solvent complex, metal complex (except one with any of $Fe^{2+}$, $Fe^{3+}$, $Co^{2+}$), solvent complex, and prodrug thereof.

The compound of the invention can exist as a mixture of its cis/trans isomers at the N=C bond connecting the 1-pyridine-2-yl moiety with the iminofluoren-2-yl moiety. Since the rate of isomerization at physiological conditions is substantial the isomers are presumed to exert a similar or even substantially the same pharmacological effect on the body.

The compound of the invention is a cell permeable iron chelator. While not wishing to bound by theory, the inventors believe that the anti-cancer effect of the compound of the invention is based on its iron-chelating properties.

The compound of the invention exhibits a cytotoxic effect in a number of in-vitro and in-vivo models. The cytotoxic effect resides in the reduction of mitochondrial respiration. It is known that colon cancer tissue contains glucose at concentrations of ~10% of that of normal tissue, and it is suggested that cancer tissue depends on aerobic respiration via the Krebs cycle (Hirayama A et al., Cancer Res 69 (2009) 4918-4925). In an in-vitro HCT116 colon cancer multicellular spheroid model the compound of the invention produces cell death corresponding to a survival index (SI) of 50% or less at a concentration of 10 µM/L. In this application, limitation of cell survival to 50% or less at a concentration of 10 µM/L by a chemical compound is considered to be a substantial cytotoxic effect and so termed. The cytotoxic activity to spheroids indicates that the compound of the invention affects both proliferating and quiescent cell populations. While the compound of the invention also affects cell proliferation of monolayer HCT116 colon cancer cell culture in high glucose medium under normoxic conditions, glucose starvation increases anti-proliferative activity.

The compound of the invention induces mitochondrial dysfunction and increases dependency on glucose. Depletion of glucose increases the sensitivity of cancer cells to the compound of the invention resulting in increased cytotoxicity and apoptosis.

According to the present invention is disclosed the use of the compound of the invention for treating a solid cancer tumour in a person. According to a preferred aspect the cell permeable iron chelator of the invention is preferably used in combination with an autophagy inhibiting agent for such treatment.

According to another preferred aspect of the invention is disclosed a pharmaceutical composition comprising the iron chelator of the invention and a pharmaceutical carrier. The pharmaceutical composition of the invention can be administered by any suitable route, such perorally or parenterally. Suitable carriers comprise, for instance, dimethyl sulfoxide and aqueous media, such as mixtures comprising dimethyl sulfoxide and water. Preferred fluid carriers are those capable of dissolving the compound of the invention. Other preferred fluid carriers, in particular aqueous carriers, are those comprising the compound of the invention in finely dispersed form, such as in form of microparticles of a size of 10 μm or smaller.

According to still another preferred aspect of the invention is disclosed a method of treating a solid cancer in a person, comprising administering to the person a pharmacologically effective dose of the iron chelator of the invention or a pharmaceutically acceptable salt, complex of prodrug thereof. The pharmacologically effective dose is preferably administered comprised by the pharmaceutical composition of the invention.

According to a further preferred aspect of the invention is disclosed a method of treating a solid cancer in a person, comprising starving the cancer of glucose and administering to the person a pharmacologically effective dose of the iron chelator of the invention or a pharmaceutically acceptable salt, complex of prodrug thereof.

The compound of the invention induces an autophagic response in vitro and in vivo. Hence, it is preferred to administer the compound of the invention in combination with an autophagy inhibiting agent. A preferred autophagy inhibiting agent is chloroquine. In view of this aspect is disclosed the use an autophagy inhibiting agent and a cell permeable iron chelator in combination in the treatment of a solid tumour. With "in combination" is understood the administration of the autophagy inhibiting agent and the cell permeable iron chelator in a close temporal relationship, such as at the same time or within a period of up to one day and even one week. The autophagy inhibiting agent and the cell permeable iron chelator can be administered in form of a pharmaceutical composition comprising them or in form of separate pharmaceutical compositions. If administered in form of a pharmaceutical composition, the combination comprises a pharmaceutically acceptable carrier.

In the combination of the autophagy inhibiting agent and the cell permeable iron chelator, the autophagy inhibiting agent is preferably selected from chloroquine. Other preferred autophagy inhibiting agents comprise hydroxychloroquine, 3-methyladenine, adenosine, bafilomycin A1,5-amino-4-imidazole carboxamide riboside, wortmannin, and viniblastine.

Further autophagy inhibitors for use in the invention are those of the general formula II

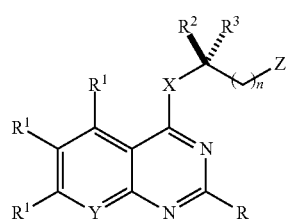

II disclosed in WO 2011011522 A2, which is incorporated herein by reference.

According to the present invention is also disclosed a method of treating a solid tumour in a person affected by cancer, the method comprising administering to said person a pharmacologically effective dose of the combination of autophagy inhibiting agent and cell permeable iron chelator of the invention in a close temporal relationship, such as at the same time or within one day or one week. Administration may be by any suitable route, such as parenteral or per-oral in form of separate pharmaceutical combinations, one comprising the autophagy inhibitor and a pharmaceutically acceptable carrier, for instance dimethyl sulfoxide, or in a single pharmaceutical combination when administered at the same time, comprising a pharmaceutically acceptable carrier such as dimethyl sulfoxide.

According to a still further preferred aspect of the invention is disclosed a method of treating a solid cancer in a person, comprising administering to the person the combination of autophagy inhibiting agent and cell permeable iron chelator in pharmacologically effective dose, either simultaneously or in a close timely relationship, such as within an hour or a day or a week. Administration is preferably in form of the pharmaceutical composition(s) disclosed above, and by the parenteral or peroral or other suitable route.

The invention will now be described in more detail by reference to a number of preferred embodiments illustrated in a drawing comprising a number of figures.

SHORT DESCRIPTION OF THE FIGURES

FIGS. 1a-1l illustrate the cytotoxicity of the compound of the invention in a HCT116 colon carcinoma cell model;

FIGS. 2a-2h illustrate the absence of substantial cytotoxicity in compounds not comprised by the invention but being of similar structure.

DESCRIPTION OF PREFERRED EMBODIMENTS

Materials and Methods
Compounds of the Invention

Exemplary compounds (Table 1) of the general formula I of the invention were prepared.

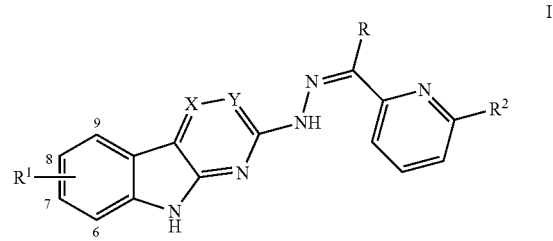

I

TABLE 1

Exemplary compounds of the invention

| Compound # | R | $R^1$ | $R^2$ | X | Y |
|---|---|---|---|---|---|
| 1 | $CH_3$ | 7-Cl | H | N | N |
| 2 | $CH_3$ | 6-Cl | H | N | N |
| 3 | $CH_3$ | 8-$OCH_3$ | H | N | N |
| 4 | $CH_3$ | 8-$OCF_3$ | H | N | N |
| 5 | $CH_3$ | 6-$CH_3$, 8-$CH_3$ | H | N | N |

TABLE 1-continued

Exemplary compounds of the invention

| Compound # | R | R[1] | R[2] | X | Y |
|---|---|---|---|---|---|
| 6 | $CH_3$ | 9-Br | H | N | N |
| 7 | $CH_3$ | 8-Cl | H | N | N |
| 8 | $CH_3$ | 8-$CH_3$ | H | N | N |
| 9 | $CH_2CH_3$ | 6-$CH_3$ | H | N | N |
| 10 | $CH_2C(CH_3)_3$ | 6-$CH_3$ | H | N | N |
| 11 | H | 6-$CH_3$ | H | CH | CH |

Table 2 shows a number of novel compounds of the general formula II not comprised by the invention. Their cytotoxicity is low or essentially lacking. They were prepared for comparison reasons.

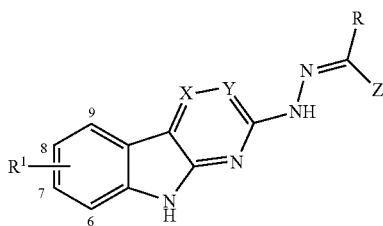

II

TABLE 2

Exemplary compounds not comprised by the invention

| Compound # | R | R[1] | X | Y | Z |
|---|---|---|---|---|---|
| 12 | $CH_3$ | 6-$CH_3$ | N | N | phenyl |
| 13 | $CH_3$ | 6-$CH_3$ | N | N | 2-(6-methoxypyridyl) |
| 14 | $CH_3$ | 6-$CH_3$ | N | N | 3-pyridyl |
| 15 | $CH_3$ | 6-$CH_3$ | N | N | 4-pyridyl |
| 16 | $C(CF_3)$ | 6-$CH_3$ | N | N | 2-pyridyl |
| 17 | $C(CH_3)_3$ | 6-$CH_3$ | N | N | 2-pyridyl |
| 18 | $CH(CH_3)_2$ | 6-$CH_3$ | N | N | 2-pyridyl |
| 19 | $CH_3$ | 6-$CH_3$ | C | C | 3-pyridyl |

General Methods

All solvents used were of HPLC grade or better. Anhydrous conditions were established by adding an excess of 3 Å molecular sieves to solvent at least 24 h prior to use. Low-resolution electrospray ionization mass spectra were obtained using an Agilent mass spectrometer in positive ionization mode. Flash chromatography was performed on Merck silica gel 60 (230-400 mesh). Analytical LC/MS data were obtained with an Agilent mass spectrometer; Agilent 1100 system. (a) ACE C8 column, (50×3.0 mm, 5 µM); Gradient: 10-97% acetonitrile in water/0.1% TFA, in 3 min, 1.0 ml/min. (b): Xbridge C18 column, (3.5 µm, 50×3.0 mm); gradient 10% to 97% acetonitrile in 10 mM $NH_4HCO_3$ (pH 10) in 3 min, 1 mL/min. Names of chemical structures were determined by means of Marvin Sketch 5.2.6, ChemAxon.

EXAMPLE 1

General Procedure for the Preparation of the 5H-[1,2,4]triazino[5,6-b]indol-3-yl-hydrazine Intermediates Used in the Synthesis of Compounds of the Invention 1-8

Thiosemicarbazide (50 mg, 0.11 mmol), the respective isatines (0.12 mmol) and $K_2CO_3$ (23.4 mg, 0.17 mmol) were dissolved in water (1 mL) and refluxed for 1.5 hours. Then the temperature was adjusted to RT. The mixtures were acidified using HOAc and the precipitates filtered off. The mother liquors were concentrated. The crude 2H,3H,5H-[1,2,4]triazino[5,6-b]indole-3-thione derivatives were used without purification in the following step.

A mixture of the respective 2H,3H,5H-[1,2,4]triazino[5,6-b]indole-3-thione derivative (0.1 mmol) and hydrazine hydrate (10 mL) was refluxed for 4 h. On cooling a precipitate formed and was filtered off. The precipitate was washed with THF and diethyl ether, and dried at RT. The obtained 5H-[1,2,4]triazino[5,6-b]indol-3-ylhydrazine intermediates were used without further purification.

EXAMPLE 2

General Procedure for the Preparation of Compounds of the Invention 1-8

The respective 5H[1,2,4]triazino[5,6-b]indol-3-ylhydrazine intermediate (0.1 mmol) was suspended in 5% of acetic acid in water (1 mL) and heated to 50° C. To the warm suspension 2-acetylpyridine (0.50 mL) was added and the reaction kept at 50° C. for 3 h. The reaction mixture was filtered. The solid products were washed thoroughly with EtOH and dried at RT.

2-[(1E)-1-(2-{7-Chloro-5H-[1,2,4]triazino[5,6-b]indol-3-yl}hydrazin-1-ylidene)ethyl]pyridine (compound 1). Purity 98% (major isomer); LC/MS: rt 1.7760 (major isomer), 1.945 (minor isomer), MS ESI$^+$/MS ESI$^+$ ms/z 338 [M+H]$^+$.

2-[(1E)-1-(2-{6-Chloro-5H-[1,2,4]triazino[5,6-b]indol-3-yl}hydrazin-1-ylidene)ethyl]pyridine (compound 2). Purity 96% (major isomer); LC/MS: rt 1.667 (major isomer), 1.868 (minor isomer), MS ESI$^+$/MS ESI$^+$ ms/z 338 [M+H]$^+$.

2-[(1E)-1-(2-{8-Methoxy-5H-[1,2,4]triazino[5,6-b]indol-3-yl}hydrazin-1-ylidene)ethyl]-pyridine (compound 3). Purity 99%; LC/MS: rt 1.661 (major isomer); MS ESI$^+$/MS ESI$^+$ ms/z 334 [M+H]$^+$.

2-[(1E)-1-{2-[8-(Trifluoromethoxy)-5H-[1,2,4]triazino[5,6-b]indol-3-yl]hydrazin-1-ylidene}ethyl]pyridine (compound 4). Purity 99% (major isomer), 2.166 (minor isomer); MS ESI$^+$/MS ESI$^+$ ms/z 388 [M+H]$^+$.

2-[(1E)-1-(2-{6,8-Dimethyl-5H-[1,2,4]triazino[5,6-b]indol-3-yl}hydrazin-1-ylidene)ethyl]pyridine (compound 5). Purity 92% (major isomer); LC/MS: rt 2.016 (major isomer), 1.878 (minor isomer); MS ESI$^+$/MS ESI$^+$ ms/z 332 [M+H]$^+$.

2-[(1E)-1-(2-{9-Bromo-5H-[1,2,4]triazino[5,6-b]indol-3-yl}hydrazin-1-ylidene)ethyl]pyridine (compound 6). Purity 99% (major isomer); LC/MS: rt 1.744 (major isomer), 1.927 (minor isomer); MS ESI$^+$/MS ESI$^+$ ms/z 383/385 [M+H]$^+$.

2-[(1E)-1-(2-{8-Chloro-5H-[1,2,4]triazino[5,6-b]indol-3-yl}hydrazin-1-ylidene)ethyl]pyridine (compound 7). Purity 98%; LC/MS: rt 1.800; MS ESI$^+$/MS ESI$^+$ ms/z 338/340 [M+H]$^+$.

2-[(1E)-1-(2-{9-Methyl-5H-[1,2,4]triazino[5,6-b]indol-3-yl}hydrazin-1-ylidene)ethyl]pyridine (compound 8). Purity 92% (major isomer); LC/MS: rt 1.790 (major isomer), 1.941 (minor isomer); MS ESI$^+$/MS ESI$^+$ ms/z 318 [M+H]$^+$.

EXAMPLE 3

Procedure for the Preparation of Compounds of the Invention 9 and 10

To a stirred suspension of 3-hydrazinyl-6-methyl-5H-[1,2,4]triazino[5,6-b]indole (20 mg, 0.09 mmol) in 5% acetic acid in water (0.67 mL) the respective ketone (0.47 mmol) was added and the reaction stirred at 50° C. for the time specified below). After cooling, water (1 mL) was added, the precipitate filtered off and washed with water/acetonitrile 1:1 and 2:1 or with diethyl ether.

2-[(1E)-1-(2-{6-Methyl-5H-[1,2,4]triazino[5,6-b]indol-3-yl}hydrazin-1-ylidene)propyl]-pyridine (compound 9). The reaction mixture was stirred at 50° C. for 1 h 15 min. A precipitate formed and was washed with diethyl ether to give the title compound in 99% purity, Method B, LC/MS: rt 1.851 (major isomer), 1.982 (minor isomer); MS ESI$^+$/MS ESI$^+$ ms/z 332 [M+H]$^+$.

2-(3,3-Dimethyl-N-{6-methyl-5H-[1,2,4]triazino[5,6-b]indol-3-}butanehydrazonoyl)pyridine (compound 10). The reaction was stirred at 50° C. for 2 hours then at 60° C. overnight and finally at 80° C. for 3 days. The solids were filtered off and washed with diethyl ether and acetonitrile to give the title product in 90% purity, Method B, LC/MS: rt 2.25, MS ESI$^+$/MS ESI$^+$ ms/z 374 [M+H]$^+$.

EXAMPLE 4

Procedure for the Preparation of 2-& 3-[(1Z)-1-(2-{8-Methyl-8H,8aH,9H-pyrido[2,3-b]indol-2-yl}hydrazin-1-ylidene)ethyl]pyridines 2,6-Dichloro-3-(3-methyl-2-nitrophenyl)pyridine. In a microwave vial, 270 mg of 2-nitro-3-bromo-toluene (1.25 mmol) and 240 mg of 2,6-dichloro-pyridine-3-boric acid (240 mg) were dissolved in 4 ml of a solvent mixture (1,4-dioxan/H$_2$O, 4:1), to which potassium carbonate (345 mg) was added, followed by addition of 28 mg of tetrakis Pd(PPh$_3$)$_4$ (0.025 mmol), degassed with nitrogen for 5 min in a microwave reactor at 100° C. for 15 min, and evaporated to remove most of solvent. The residue was dissolved in 50 ml of ethyl acetate, washed with 3×10 ml of brine, and dried over MgSO$_4$. After evaporation of the solvent the residue was purified by flash chromatography (heptane/ethyl acetate, 85:15). Pure title compound (99 mg, 28%) was obtained as a white powder. LC-MS: rt 1.803; MS ESI$^+$/MS ESI$^+$ ms/z 283 [M+H]$^+$.

2-(2,6-Dichloropyridin-3-yl)-6-methylaniline. In a glass flask, 282 mg of 2,6-dichloro-3-(3-methyl-2-nitrophenyl) pyridine (1 mmol) was dissolved in 20 ml of methanol, then 325 mg of zinc dust (5 mmol) and 570 μl of acetic acid (10 mmol) was added. The mixture was stirred at room temperature for 30 min, then at 75° C. for 1 hr. After the reaction was finished, the reaction mixture was filtered to remove precipitate, and the precipitate washed with 20 ml of methanol, then evaporated to remove the bulk of solvent. The residue was dissolved in ethyl acetate and brine, and purified by chromatography (heptane/ethyl acetate, 90:10). LC-MS: rt 1.734; MS ESI$^+$/MS ESI$^+$ ms/z 253 [M+H]$^+$.

2-Chloro-8-methyl-8H,8aH,9H-pyrido[2,3-b]indole. 2-(2,6-Dichloropyridin-3-yl)-6-methylaniline (154 mg, 0.61 mmol), 59 mg of copper iodate, 70 mg of L-proline (0.61 mmol) and 398 mg of Cs$_2$CO$_3$ (1.22 mmol) were mixed with 8 ml of DMF, heated at 90° C. for 1 hr, then at 100° C. for 5 h, diluted with ethyl acetate, and washed with brine to remove most of DMF and base. The residue was purified by flash chromatography (heptane/ethyl acetate 90:10), yield 49 mg. LC-MS: rt 1.730; MS ESI$^+$/MS ESI$^+$ ms/z 217 [M+H]$^+$.

2-Hydrazinyl-8-methyl-8H,8aH,9H-pyrido[2,3-b]indole. 2-Chloro-8-methyl-8H,8aH,9H-pyrido[2,3-b]indole (33 mg, 0.15 mmol) was suspended in 0.8 ml of hydrazine hydride, and stirred at 85° C. over the weekend. The starting material had been fully converted. The mixture was cooled to form a precipitate. The crude product was filtered off to yield 21 mg of crude title compound, which was used in the next step without purification. LC-MS: rt 1.320; MS ESI$^+$/MS ESI$^+$ ms/z 213 [M+H]$^+$.

3-[(1Z)-1-(2-{8-Methyl-8H,8aH,9H-pyrido[2,3-b]indol-2-yl}hydrazin-1-ylidene)ethyl]-pyridine (compound 19). 2-Hydrazinyl-8-methyl-8H,8aH,9H-pyrido[2,3-b]indole (10 mg, 0.05 mmol) was suspended in 0.5 ml of 5% acetic acid comprising 27 μl of 3-acetyl pyridine and stirred at RT for 30 min, then at 50° C. for another 30 min, After cooling to RT the precipitate that had been formed was collected and purified by prep. HPLC, (C18 column, gradient 45-85% methanol in 10 mM NH$_4$HCO$_3$ (pH 10), 25 ml/min.). The title compound (1 mg) was obtained in 90% purity. LC-MS: A, rt 1.674, B rt 2.314; MS ESI$^+$/MS ESI$^+$ ms/z 316 [M+H]$^+$.

2-[(1Z)-1-(2-{8-Methyl-8H, 8aH, 9H-pyrido[2,3-b]indol-2-yl}hydrazin-1-ylidene)ethyl]-pyridine (compound 11). 2-Hydrazinyl-8-methyl-8H,8aH,9H-pyrido[2,3-b]indole (10 mg, 0.05 mmol) was suspended in a mixture of 0.5 ml of 5% acetic acid and 28 μl of 2-acetyl pyridine, and stirred at RT for 30 min. The temperature was raised 50° C. and the mixture stirred for another 30 min, then cooled to RT. A precipitate formed, which was purified by prep. HPLC, (C18 column, gradient 45-85% methanol in 10 mM NH$_4$HCO$_3$ (pH 10), at 25 ml/min). The title compound (1 mg) was obtained in 95% purity. LC-MS: A, rt 1.805, B, rt 2.608; MS ESI$^+$/MS ESI$^+$ ms/z 316 [M+H]$^+$.

Abbreviations: ACN, acetonitrile; DCM, dichloromethane; DMF, dimethyl formamide; rt, retention time; RT, room temperature; LC, liquid chromatography; SI, survival index

EXAMPLE 5

Cell Culture, Generation of MCS and Determination of Cytotoxicity In-Vitro

HCT116 colon carcinoma cells were maintained in McCoy's 5A modified medium/10% fetal calf serum at 37° C. in 5% CO$_2$. MCS were prepared using a modification the method of Herrmann R et al., *Screening for compounds that induce apoptosis of cancer cells grown as multicellular spheroids.* J Biomol Screen 2008; 13:1-8. A cell suspension containing 10,000 cells (200 μl) was added to each well of poly-HEMA coated 96 well plates. The wells were then overfilled by adding an additional 170 μl media to acquire a convex surface curvature. Plasticine spacers (3 mm) were placed in the corners of each plate to prevent the lids from touching the media. The plates were then inverted in order to allow the cells to sediment to the liquid/air interface and incubated in gentle shaking. After 24 h incubation the plates were returned to normal. First excess media was removed by aspiration and then plasticine spacers. The plates were incubated for 4 days prior to drug treatment. After 24 hours of drug treatment, NP40 was added to the culture medium to a concentration of 0.1% to extract caspase-cleaved K18 from MCS and to include material released to the medium from dead cells. Caspase cleaved keratin-18 (K18-Asp396) was determined using 25 mL medium/extract using the M30 CytoDeath ELISA assay (a variant of the M30-Apoptosense® ELISA (Hägg M et al., *A novel high-through-put assay for screening of pro-apoptotic drugs. Invest New Drugs* 2002; 20:253-9) developed for in-vitro use (Peviva A B, Bromma, Sweden)). Viability measurements were performed by the acid phosphatase (APH) method described by Friedrich et al., *A reliable tool to determine cell viability in complex 3-d culture: the acid phosphatase assay.* J Biomol Screen 2007; 12:92537. Background activity was subtracted. The cytotoxicity of compounds of the invention (FIGS. 1a-1l) and of structurally related compounds not comprised by the invention (FIGS. 2a-2h) was determined in the HCT116 colon carcinoma cell model and expressed by the survival index of the cells in dependence on compound concentration.

EXAMPLE 6

The Compound of the Invention Exhibits Cytotoxicity In Vivo

The compound of the invention (compound 11) was injected intravenously in NMRI mice. At the maximally tolerated dose (MTD) of 16 mg/kg, an initial plasma concentration of ~100 μM was observed, >10-fold the $IC_{50}$ of tumor cell lines and primary patient colorectal cancer cells in vitro. The compound was rapidly distributed and finally eliminated with a half-life of 4~5 h. The systemic toxicity of the compound of the invention is low. Doses up to 4.5 mg/kg did not produce noteworthy changes in the animal's plasma parameters such as liver ALT, blood glucose and total protein nor did they prevent the animals from gaining weight.

EXAMPLE 7

The Compound of the Invention is a Cell Permeable Iron Chelator

To test whether the cytotoxic activity of the compound of the invention is dependent on iron depletion, iron chloride was added to HCT116 cells prior to the addition of the compound of the invention. Iron chloride was found to totally abrogate the effect of the compound of the invention, both on HCT116 cells expressing wtp53 as on HCT116 cells where the p53 gene has been disrupted.

EXAMPLE 8

Pharmaceutical Composition

The compound of the invention is dissolved in an organic solvent, for instance methanol, comprising at least 2 molar equivalents of hydrochloric acid. By adding a second solvent, for instance ethanol, the dihydrochloride of the compound precipitates from the solution as such or as a complex with the precipitating solvent, for instance as compound.2 HCl.EtOH. The dihydrochloride/ethanol complex is a preferred embodiment of the compound of the invention for use in a pharmaceutical composition. It is preferably used in form of a cryoprecipitate. If desired, the cryoprecipitate can be incorporated into a tablet in combination with standard powderous pharmaceutical excipients, such as mannitol, starch, and microcellulose. The excipients should be of low basicity. When suspended in water, they should not raise the pH above 7.0 but rather provide a pH from 5.0-7.0.

Stability studies at room temperature were conducted with from 0.1 mg/L to 15 mg/L of the dihydrochloride/ethanol complex in 5% aqueous mannitol (to provide for isotonicity). Weaker solutions were found to degrade more rapidly. For instance, about 2.5% compound 11 is degraded after storage for 100 h of a solution comprising 15 mg compound per liter, while about 5% of the compound is degraded in a solution comprising 2 mg compound per liter, and about 13 of the compound in a solution comprising 0.1 mg compound per liter. HPLC reveals the formation of a number of degradation products.

The invention claimed is:

1. Cytotoxic compound of formula I, wherein R is H, methyl or methylene substituted by $C_1$-$C_4$ straight or branched alkyl, $R^1$ is selected from the group consisting of H, $C_1$-$C_4$ straight or branched alkyl, methoxy, methoxy substituted by from one to three fluorine, and halogen; $R^2$ is H or $C_1$-$C_4$ straight or branched alkyl; X is CH or N; and Y is CH or N; provided that R is methylene substituted by $C_1$-$C_4$ straight or branched alkyl if $R^1$ is H, halogen, or $C_1$-$C_4$ alkyl, $R^2$ is H or $C_1$-$C_4$ straight or branched alkyl, X is N and Y is N,

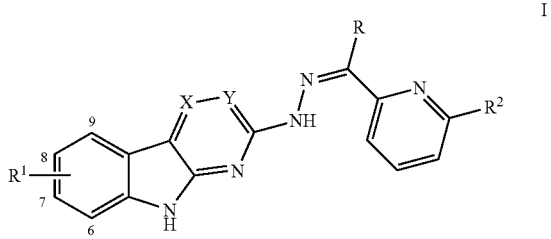

or a pharmaceutically acceptable salt of the compound of formula I, or a pharmaceutically acceptable metal complex of the compound of formula I with a metal other than $Fe^{2+}$, $Fe^{3+}$, or $Co^{2+}$.

2. The compound of claim 1, or the pharmaceutically acceptable salt thereof or the pharmaceutically acceptable metal complex thereof, wherein $R^2$ is H.

3. The compound of claim 2, or the pharmaceutically acceptable salt thereof or the pharmaceutically acceptable metal complex thereof, wherein R=H, $R^1$=6-$CH_3$, $R^2$=H, and X and Y=CH; wherein R=$CH_2C(CH_3)_3$, $R^1$=6-$CH_3$, $R^2$=H, and X and Y=N; or wherein R=$CH_2CH_3$, $R^1$=6-$CH_3$, $R^2$=H, and X and Y=N.

4. A mixture of cis- and trans-isomers of the compound of claim 1.

5. A pharmaceutically acceptable salt or a pharmaceutically acceptable metal complex with a metal other than $Fe^{2+}$, $Fe^{3+}$, or $Co^{2+}$, of the compound of claim 1.

6. A pharmaceutically acceptable salt of the compound of claim 1 selected from hydrochloride salt and di-hydrochloride salt.

7. Pharmaceutical composition comprising the compound of claim 1, or the pharmaceutically acceptable salt thereof or the pharmaceutically acceptable metal complex thereof, and a pharmaceutically acceptable carrier.

8. The compound of claim 3, or the pharmaceutically acceptable salt thereof or the pharmaceutically acceptable metal complex thereof, wherein R=$CH_2C(CH_3)_3$, $R^1$=6-$CH_3$, $R^2$=H, and X and Y=N.

9. The compound of claim 3, or the pharmaceutically acceptable salt thereof or the pharmaceutically acceptable metal complex thereof, wherein R=$CH_2CH_3$, $R^1$=6-$CH_3$, $R^2$=H, and X and Y=N.

10. A pharmaceutically acceptable salt of the compound of claim 3 selected from hydrochloride salt and di-hydrochloride salt.

11. A pharmaceutically acceptable salt of the compound of claim 8 selected from hydrochloride salt and di-hydrochloride salt.

12. A pharmaceutically acceptable salt of the compound of claim 9 selected from hydrochloride salt and di-hydrochloride salt.

13. A method of treating a solid colon cancer tumour in a person, comprising administering to the person a pharmacologically effective dose of the compound of claim 3, or the pharmaceutically acceptable salt thereof or the pharmaceutically acceptable metal complex thereof.

14. A method of treating a solid colon cancer tumour in a person, comprising administering to the person a pharmacologically effective dose of the compound of claim 8, or the pharmaceutically acceptable salt thereof or the pharmaceutically acceptable metal complex thereof.

15. A method of treating a solid colon cancer tumour in a person, comprising administering to the person a pharmacologically effective dose of the compound of claim 9, or the pharmaceutically acceptable salt thereof or the pharmaceutically acceptable metal complex thereof.

16. Cytotoxic compound of formula I, wherein R is H, methyl or methylene substituted by $C_1$-$C_4$ straight or branched alkyl, $R^1$ is selected from the group consisting of $C_1$-$C_4$ straight or branched alkyl, methoxy, methoxy substituted by from one to three fluorine, and halogen; $R^2$ is H or $C_1$-$C_4$ straight or branched alkyl; X is CH or N; and Y is CH or N; provided that R does not comprise H or methyl if $R^1$ is $C_1$-$C_4$ alkyl, $R^2$ is H or $C_1$-$C_4$ straight or branched alkyl, X is N and Y is N,

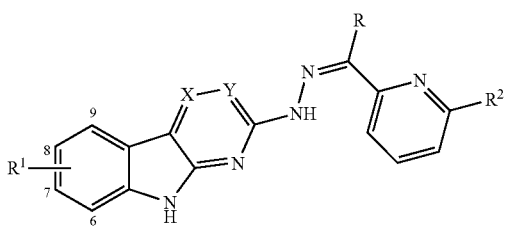

and wherein the cytotoxic compound is additionally substituted by a $C_1$-$C_4$ straight or branched alkyl at one of positions 6, 7, 8 or 9 not substituted by $R^1$, or a pharmaceutically acceptable salt of the compound of formula I, or a pharmaceutically acceptable metal complex of the compound of formula I with a metal other than $Fe^{2+}$, $Fe^{3+}$, or $Co^{2+}$.

17. A method of treating a solid colon cancer tumour in a person, comprising administering to the person a pharmacologically effective dose of a compound of formula I, wherein R is H, methyl or methylene substituted by $C_1$-$C_4$ straight or branched alkyl, $R^1$ is selected from the group consisting of H, $C_1$-$C_4$ straight or branched alkyl, methoxy, methoxy substituted by from one to three fluorine, and halogen; $R^2$ is H or $C_1$-$C_4$ straight or branched alkyl; X is CH or N; and Y is CH or N; provided that R does not comprise H or methyl if $R^1$ is H or $C_1$-$C_4$ alkyl, $R^2$ is H or $C_1$-$C_4$ straight or branched alkyl, X is N and Y is N,

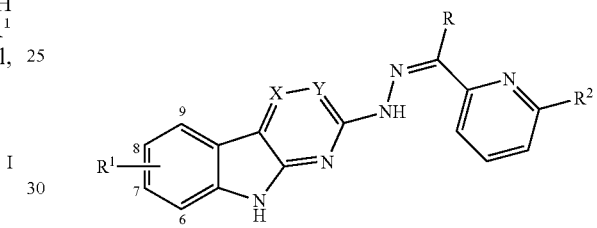

or a pharmaceutically acceptable salt of the compound of formula I, or a pharmaceutically acceptable metal complex of the compound of formula I with a metal other than $Fe^{2+}$, $Fe^{3+}$, or $Co^{2+}$.

\* \* \* \* \*